United States Patent [19]

Richardson et al.

[11] Patent Number: 4,510,148
[45] Date of Patent: Apr. 9, 1985

[54] 2-HETEROCYCLIC-1,3-BIS(1H-1,2,4-TRIAZOL-1-YL)-PROPAN-2-OLS AS ANTIFUNGAL AGENTS

[75] Inventors: Kenneth Richardson, Canterbury; Kelvin Cooper, Ramsgate, both of England

[73] Assignee: Pfizer Inc., New York, N.Y.

[21] Appl. No.: 499,073

[22] Filed: May 27, 1983

[30] Foreign Application Priority Data

Jun. 12, 1982 [GB] United Kingdom ............... 8217114

[51] Int. Cl.³ ................... A01N 43/64; A01N 43/78; C07D 401/14; C07D 405/14
[52] U.S. Cl. .................................. 514/340; 514/383; 548/179; 548/262; 546/344; 549/78; 549/497
[58] Field of Search ............... 548/179, 262; 546/276; 424/263, 269, 270

[56] References Cited

U.S. PATENT DOCUMENTS

| 3,658,813 | 4/1972 | Godefroi et al. | 548/341 |
| 4,328,028 | 5/1982 | Rentzea et al. | 71/92 |
| 4,399,143 | 8/1983 | Yokomichi et al. | 546/276 |
| 4,404,216 | 9/1983 | Richardson | 548/262 |
| 4,411,687 | 10/1983 | Zeeh et al. | 546/276 |

FOREIGN PATENT DOCUMENTS 0044605 1/1982 European Pat. Off. .
2099818 12/1982 United Kingdom .

Primary Examiner—Alton D. Rollins
Attorney, Agent, or Firm—Charles J. Knuth; Albert E. Frost; James M. McManus

[57] ABSTRACT

Compounds of the formula

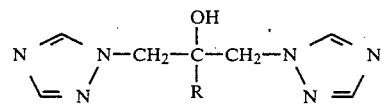

wherein R is thienyl, mono-, di- and trihalothienyl, furyl, 2-benzothiazolyl, pyridyl or chloropyridyl and their pharmaceutically acceptable salts are useful agents for combating fungal infections in animals, including humans.

2 Claims, No Drawings

2-HETEROCYCLIC-1,3-BIS(1H-1,2,4-TRIAZOL-1-YL)-PROPAN-2-OLS AS ANTIFUNGAL AGENTS

BACKGROUND OF THE INVENTION

This invention relates to novel 1,3-bis(1H-1,2,4-triazol-1-yl)propan-2-ol derivatives which are useful in treating fungal infections in animals, including humans.

British Patent Application 2,099,818 claims 2-(2',4'-difluorophenyl)-1,3-bis(1H-1,2,4-triazol-1-yl)propan-2-ol and salts thereof as useful antifungal agents.

2-Substituted-1,3-bis(1H-1,2,4-triazol-1-yl and 1H-imidazol-1-yl)propan-2-ols are described in European Patent Application 44,605 as being useful antifungal agents.

SUMMARY OF THE INVENTION

The compounds of the present invention are of the formula

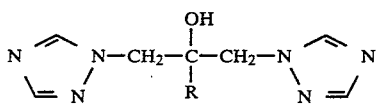

and the pharmaceutically acceptable salts thereof, wherein R is thienyl, mono-, di- or trihalothienyl, furyl, 2-benzothiazolyl, pyridyl or chloropyridyl.

A preferred group of compounds are those wherein R is bromothienyl; especially preferred is 5-bromo-2-thienyl.

A second preferred group of compounds are those wherein R is chloropyridyl; especially preferred is 5-chloro-2-pyridyl.

The invention also includes a pharmaceutical composition comprising the aforementioned compounds of the present invention together with a pharmaceutically acceptable diluent or carrier.

Also included as part of the present invention is a method for treating fungal infections in a human being, which comprises administering to said human being an antifungal amount of an aforementioned compound of the present invention or a pharmaceutically acceptable salt thereof.

The term "halo" as employed as a substituent is meant chloro or bromo.

DETAILED DESCRIPTION OF THE INVENTION

The compounds of formula I are obtained by the following process:

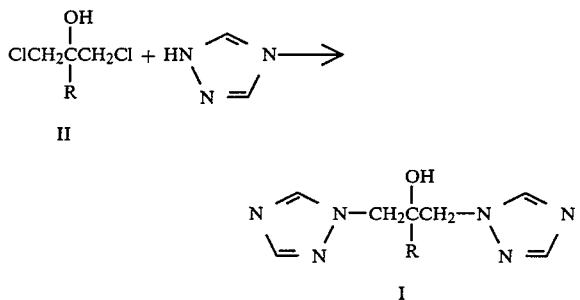

It is preferred that the reaction be carried out in a reaction-inert solvent. By such a solvent is meant one which does not react to any appreciable extent in a detrimental manner with the reactants or product and one which solubilizes to some extent the reactants. A preferred solvent is dimethylformamide or dimethylacetamide.

The reactants, one mole of II and at least two moles of 1,2,4-triazole, are contacted in the reaction solvent in the presence of two equivalents of an acid scavenger, such as potassium carbonate.

Reaction time will vary with the reaction temperature and reactivity of the reactants. At the preferred reaction temperature of about 80° C. the reaction is essentially complete in about two hours.

The product is isolated by evaporation of the solvent followed by extraction with an organic solvent, such as ethyl acetate. The crude product is purified by conventional means, such as recrystallization or column chromatography.

The starting materials of formula (II) can be obtained by conventional methods from the appropriate heterocyclic compounds. In a typical case they are prepared by reacting a halo-substituted derivative of the desired heterocyclic compound with butyl lithium to generate the anion, which is then reacted with dichloroacetone as shown in the following reaction scheme.

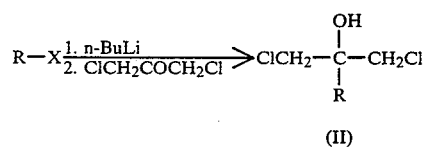

wherein X is chloro, bromo or iodo.

It is not generally necessary to isolate the product (II) but it can be reacted directly with triazole as previously described to give the compound of formula (I).

The halo-substituted heterocyclic compounds (III), preferably the bromo derivatives, are generally known compounds which are either commercially available or they are prepared by conventional methods in accordance with literature precedents.

Pharmaceutically acceptable acid addition salts of the compounds of the formula (I) include those formed from strong acids which form non-toxic acid addition salts, such as hydrochloric, hydrobromic, sulphuric, nitric, oxalic and methane sulphonic acids.

The salts may be obtained by conventional procedures, e.g., by mixing solutions containing equimolar amounts of the free base and desired acid, and the required salt is collected by filtration, if insoluble, or by evaporation of the solvent.

The compounds of the formula (I) and their pharmaceutically acceptable salts are anti-fungal agents, useful in combating fungal infections in animals, including humans. For example they are useful in treating topical fungal infections in man caused by, among other organisms, species of Candida, Trichophyton, Microsporum or Epidermophyton, or in mucosal infections caused by Candida albicans (e.g., thrush and vaginal candidiasis). They may also be used systemically in the treatment of systemic fungal infections caused by, for example, Candida albicans, Cryptococcus neoformans, Aspergillus Fumigatus, Coccidioides, Paracoccidioides, Histoplasma or Blastomyces.

The in vitro evaluation of the anti-fungal activity of the compounds can be performed by determining the minimum inhibitory concentration (m.i.c.) of the test compounds in a suitable medium at which growth of the particular micro-organism fails to occur. In practice, a series of agar plates, each having the test compound incorporated at a particular concentration are inoculated with a standard culture of, for example, *Candida albicans* and each plate is then incubated for 48 hours at 37° C. The plates are then examined for the presence or absence of growth of the fungus and the appropriate m.i.c. value is noted. Other micro-organisms used in such tests can include *Cryptococcus neoformans, Aspergillus fumigatus,* Trichophyton spp; Microsporum; *Epidermophyton floccosum, Coccidioides immitis,* and *Torulopsis glabrata*.

The in vivo evaluation of the compounds can be carried out at a series of dose levels by intraperitoneal or intravenous injection or by oral administration, to mice which are inoculated with a strain of *Candida albicans*. Activity is based on the survival of a treated group of mice after the death of an untreated group of mice following 48 hours observation. The dose level at which the compound provides 50% protection against the lethal effect of the infection is noted.

For human use, the anti-fungal compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

For oral and parenteral administration to human patients, the daily dosage level of the anti-fungal compounds of the formula (I) will be from 0.1 to 10 mg/kg (in divided doses) when administered by either the oral or parenteral route. Thus tablets or capsules of the compounds can be expected to contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the anti-fungal compounds of formula (I) may be administered in the form of a suppository or pessary, or they may be applied topically in the form of a lotion, solution, cream, ointment or dusting powder. For example, they may be incorporated into a cream consisting of an aqueous emulsion of polyethylene glycols or liquid paraffin; or they may be incorporated, at a concentration between 1 and 10%, into an ointment consisting of a white wax or white soft paraffin base together with such stabilizers and preservatives as may be required.

The compounds of the formula (I) and their salts also have activity against a variety of plant pathogenic fungi, including for example various rusts, mildews and moulds, and the compounds are thus useful as agricultural fungicides for treating plants and seeds to eradicate or prevent such diseases.

The following Examples illustrate the invention.

EXAMPLE 1

General Purpose (a) Preparation of dichloropropanol derivatives (formula II)

A solution of n-butyl lithium in hexane (12.5 ml., 1.55 molar, 19.4 mmole) was added under nitrogen to a stirred solution of the haloheterocyclic compound (20 mmole) in dry diethyl ether (40 ml.) at −78° C. over a period of 15 minutes. The mixture was stirred at −78° C. for a further 15 minutes after the addition was complete and a solution of dichloroacetone (2.3 g., 20 mmole) in diethyl ether (25 ml.) was then added over a period of 15 minutes. After a further 30 minutes at −78° C. a solution of acetic acid (2 ml.) in diethyl ether (10 ml.) was added followed by water (15 ml.) and the mixture allowed to warm to room temperature. The mixture was neutralized with aqueous sodium carbonate solution and the organic layer was separated and washed with water. The aqueous washes were extracted with diethyl ether and the combined organic layers were dried (MgSO$_4$) and evaporated to yield the desired dichloropropanol derivative.

(b) Preparation of bis-triazolylpropanol derivatives (formula I)

1,2,4-Triazole (3.3 g., 48 mmole), and anhydrous potassium carbonate (6.6 g., 48 mmole) were added to a solution of the dichloropropanol derivative (nominal 20 mmole) in dry N,N-dimethylformamide (65 ml.), and the mixture heated on an oil bath at 80° C. for 2 hours with stirring. The mixture was cooled, the solvent evaporated under reduced pressure and the residue extracted with boiling ethyl acetate (3×50 ml.). The combined extracts were evaporated to dryness and the residue chromatographed on silica eluting with an appropriate solvent (generally a mixture of chloroform, methanol and concentrated ammonium hydroxide, 32:4:1). Fractions containing the product were combined and evaporated and the product recrystallized from an appropriate solvent to yield the compound of formula (I).

EXAMPLE 2

Starting with 2-bromothiophene, and employing the procedures of Example 1(a) and 1(b), the following compound was prepared:

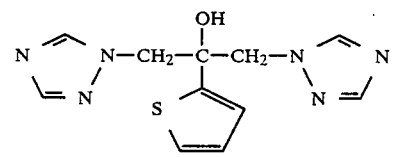

m.p.: 65°–66° C.

Anal. Calcd. for $C_{11}H_{12}OSN_6$: C, 44.9; H, 4.8; N, 28.6; Found: C, 44.9; H, 4.1; N, 29.3[1]

[1]Analyzed for monohydrate

EXAMPLES 3–13

Employing the indicated starting haloheterocyclic compound and employing the procedures of Example 1(a) and 1(b), the following compounds were prepared:

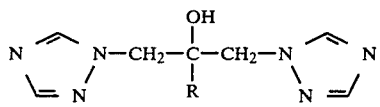

Example 3

Starting material: 2-chloro-5-iodothiophene[2]
R=5-chloro-2-thienyl
m.p.=130°–131° C.
Anal. Calcd. for $C_{11}H_{11}OSN_6Cl$: C, 42.6; H, 3.6; N, 27.1; Found: C, 42.6; H, 3.4; N, 27.4
[2]J. Metysora, et al., *Coll. Czech. Chem. Comm.*, 35, 378 (1970).

Example 4

Starting material: 2,5-dibromothiophene
R=5-bromo-2-thienyl
m.p.=147°–148° C.
Anal. Calcd. for $C_{11}H_{11}OSN_6Br$: C, 37.2; H, 3.1; N, 23.7; Found: C, 37.4; H, 3.2; N, 23.4

Example 5

Starting material: 2,3,4-trichlorothiophene[3]
R=3,4-dichloro-2-thienyl[4]
m.p.=144°–145° C.
Anal. Calcd. for $C_{11}H_{10}OSN_6Cl_2$: C, 38.3; H, 2.9; N, 24.4; Found: C, 38.7; H, 2.9; N, 25.0
[3]Prepared as described in Preparation 1.
[4]Two mmole equivalents of n-butyl lithium were used for step (a).

Example 6

Starting material: 2,3,4,5-tetrachlorothiophene
R=3,4,5-trichloro-2-thienyl
m.p.=162°–164° C.
Anal. Calcd. for $C_{11}H_9OSN_6Cl_3$: C, 34.9; H, 2.4; N, 22.2 Found: C, 35.3; H, 2.6; N, 22.1

Example 7

Starting material: 2,3-dibromothiophene
R=3-bromo-2-thienyl
m.p.=208°–209° C.
Anal. Calcd. for $C_{11}H_{11}OSN_6Br$: C, 37.2; H, 3.1; N, 23.7; Found: C, 37.3; H, 3.2; N, 24.2

Example 8

Starting material: 3-bromothiophene
R=3-thienyl[1]
m.p.=69°–71° C.
Anal. Calcd. for $C_{11}H_{12}OSN_6$: C, 44.9; H, 4.8; N, 28.6; Found: C, 44.6; H, 4.6; N, 28.8

Example 9

Starting material: 3-bromo-2-chlorothiophene
R=2-chloro-3-thienyl
m.p.=163°–165° C.
Anal. Calcd. for $C_{11}H_{11}OSN_6Cl$: C, 42.6; H, 3.6; N, 27.1; Found: C, 41.7; H, 3.4; N, 27.0

Example 10

Starting material: 3-bromofuran
R=3-furyl
m.p.=116°–117° C.
Anal. Calcd. for $C_{11}H_{12}O_2N_6$: C, 50.8; H, 4.7; N, 32.3; Found: C, 50.9; H, 4.7; N, 32.5

Example 11

Starting material: 2-bromobenzothiazole[5]
R=2-benzothiazolyl
m.p.=192°–193° C.
Anal. Calcd. for $C_{14}H_{13}OSN_7$: C, 51.4; H, 4.0; N, 30.0; Found: C, 51.4; H, 3.9; N, 30.6
[5]Prepared as described in Preparation 2

Example 12

Starting material: 2-bromopyridine
R=2-pyridyl[6]
m.p.=112°–114° C.
Anal. Calcd. for $C_{12}H_{13}ON_7$: C, 45.4; H, 4.1; N, 25.5; Found: C, 45.1; H, 4.2; N, 25.6
[6]Analyzed for the 1.25 oxalate

Example 13

Starting material: 2-bromo-5-chloropyridine[7]
R=5-chloro-2-pyridyl
m.p. 180°–181° C.
Anal. Calcd. for $C_{12}H_{12}ON_7Cl$: C, 47.1; H, 4.0; N, 32.1; Found: C, 47.2; H, 4.0; N, 32.2
[7]Prepared as described in Preparation 3

EXAMPLE 14

The following illustrate pharmaceutical compositions for the treatment of fungal infections:

(1) Capsule: 71 parts by weight of the compound of Example 12 are granulated with 3 parts maize starch and 22 parts lactose and then a further 3 parts of maize starch and 1 part magnesium stearate are added. The mixture is regranulated and filled into hard gelatin capsules.

(2) Cream: 2 parts by weight of the compound of Example 12 are dissolved in 10 parts of propylene glycol and mixed into 88 parts of a vanishing cream base.

(3) Pessary: 2 parts by weight of the compound of Example 12 are suspended in 98 parts of warm liquified suppository base which is poured into moulds and allowed to solidify.

PREPARATION 1

Preparation of 2,3,4-Trichlorothiophen

A solution of n-butyl lithium (48.3 ml. of 1.55M, 75 mmole) was added dropwise to a stirred solution of tetrachlorothiophen (16.65 g., 75 mmole) in diethyl ether (150 ml.) at −78° C. After the addition was complete the mixture was stirred at −78° C. for 1 hour and was then diluted with acetic acid (6 ml.) in diethyl ether (25 ml.). The mixture was allowed to come to room temperature and the organic phase was separated. The aqueous layer was extracted with diethyl ether and the combined organic layers were dried (MgSO4) and evaporated and residue distilled to give the desired product (10.9 g., 77%), b.p. 88°–91° at 16 mm Hg.

PREPARATION 2

Preparation of 2-bromobenzothiazole

2-Bromobenzothiazole was prepared from 2-aminobenzothiazole according to the method of Y. Mizuno, K. Adachi, K. Nakamura, *Pharm. Bill.*, 1953, 1, 319, to furnish a white crystalline solid in 49% yield, m.p. 39°–40° C.

PREPARATION 3

Preparation of 2-bromobenzothiazole

2-Bromo-5-chloropyridine was prepared from 2-amino-5-chloropyridine according to the method of L. C. Craig, *J. Amer. Chem. Soc.*, 1934, 56, 231, to furnish a white crystalline solid in 70% yield, m.p. 69°–70° C.

PREPARATION 4

Preparation of 2-bromo-3,5-dichloropyridine

2-Bromo-3,5-dichloropyridine was prepared from 2-amino-3,5-dichloropyridine according to the method of L. C. Craig, *J. Amer. Chem. Soc.*, 1934, 56, 231 to furnish a pale yellow crystalline solid in 76% yield, m.p. 37°–38° C.

We claim:

1. Compound of the formula

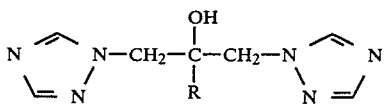

and the pharmaceutically acceptable salts thereof, wherein R is 5-chloro-2-pyridyl.

2. A pharmaceutical composition comprising a compound as claimed in claim 1 together with a pharmaceutically acceptable diluent or carrier.

* * * * *